(12) United States Patent
Galluseder et al.

(10) Patent No.: US 11,963,838 B2
(45) Date of Patent: Apr. 23, 2024

(54) PREPARING AND/OR CARING FOR A MEDICAL OR DENTAL INSTRUMENT

(71) Applicant: W&H Dentalwerk Bürmoos GmbH, Bürmoos (AT)

(72) Inventors: Florian Galluseder, Tarsdorf (AT); Michael Reiter, Elsbethen (AT)

(73) Assignee: W&H Dentalwerk Bürmoos GmbH, Bürmoos (AT)

(*) Notice: Subject to any disclaimer, the term of this patent is extended or adjusted under 35 U.S.C. 154(b) by 608 days.

(21) Appl. No.: 17/184,563

(22) Filed: Feb. 24, 2021

(65) Prior Publication Data

US 2021/0267735 A1 Sep. 2, 2021

(30) Foreign Application Priority Data

Mar. 2, 2020 (EP) .................................... 20160298

(51) Int. Cl.
*A61C 19/00* (2006.01)
*A61B 1/00* (2006.01)
*A61B 1/12* (2006.01)
*A61L 2/18* (2006.01)
*A61L 2/24* (2006.01)

(52) U.S. Cl.
CPC ........ *A61C 19/002* (2013.01); *A61B 1/00055* (2013.01); *A61B 1/00057* (2013.01); *A61B 1/00059* (2013.01); *A61B 1/125* (2013.01); *A61L 2/18* (2013.01); *A61L 2/24* (2013.01)

(58) Field of Classification Search
None
See application file for complete search history.

(56) References Cited

U.S. PATENT DOCUMENTS

2008/0199356 A1* 8/2008 Suter ..................... A61B 90/70
433/82

FOREIGN PATENT DOCUMENTS

| CA | 2127903 | | 1/1995 |
| CN | 1345208 | A | 4/2002 |
| CN | 107361872 | A | 11/2017 |
| EP | 1652488 | | 5/2006 |
| EP | 1749502 | | 2/2007 |
| EP | 2138127 | | 12/2009 |
| EP | 2514386 | | 10/2012 |
| JP | 2008514375 | A | 5/2008 |
| WO | WO2005/009271 | A1 | 2/2005 |
| WO | WO2018/073339 | A1 | 2/2018 |

OTHER PUBLICATIONS

EP 1749502 A1 translation, Apparatus for the Maintenance and the Cleaning of Medical Instruments, Helfenbein (Year: 2007).*
Search Report for European Application No. 20160298.4, dated Aug. 26, 2020.

* cited by examiner

*Primary Examiner* — Cristi J Tate-Sims
(74) *Attorney, Agent, or Firm* — Klarquist Sparkman, LLP

(57) ABSTRACT

A method for preparing and/or caring for a medical or dental instrument is defined in that the instrument jointly with a connection adapter is first connected to a first preparation and/or care device and subsequently to a second preparation and/or care device. Furthermore, a coupling device is described which is configured to connect a preparation and/or care device for a medical or dental instrument to a connection adapter. A plug-in coupling arrangement and a system are also disclosed.

20 Claims, 5 Drawing Sheets

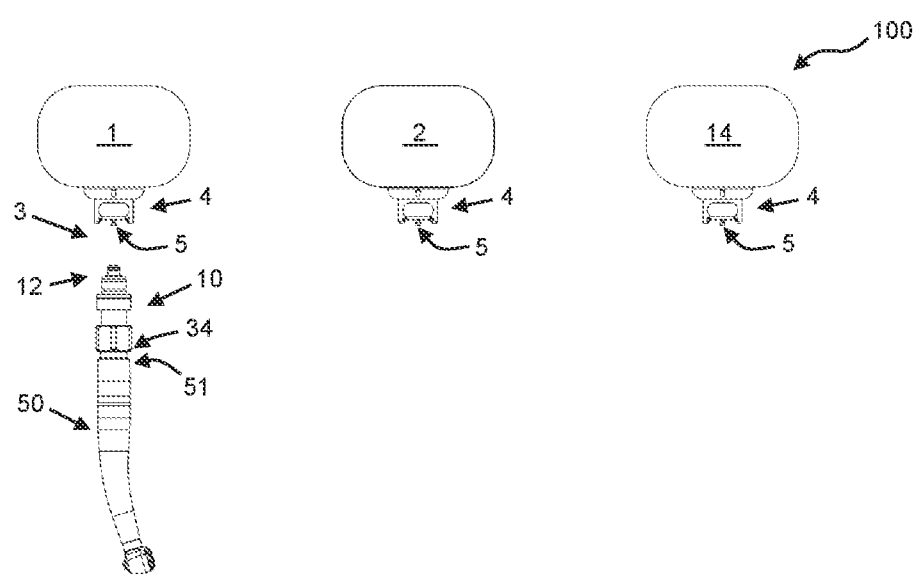
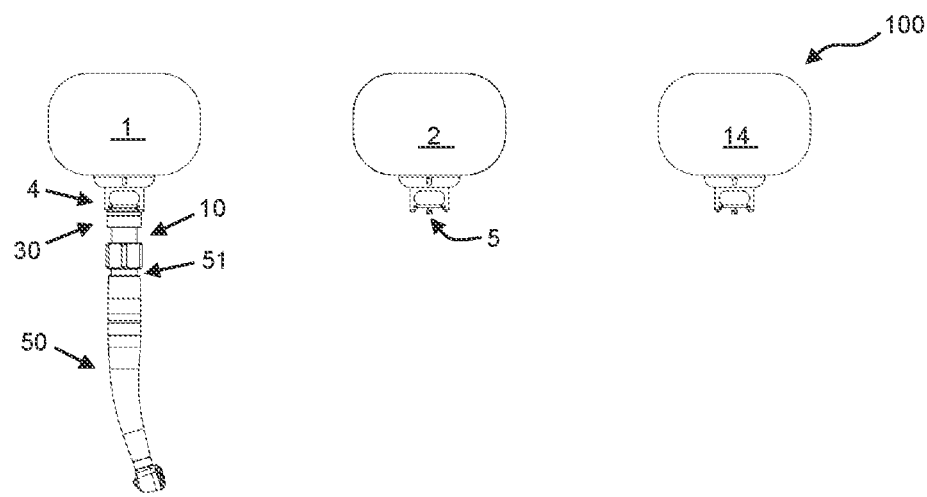
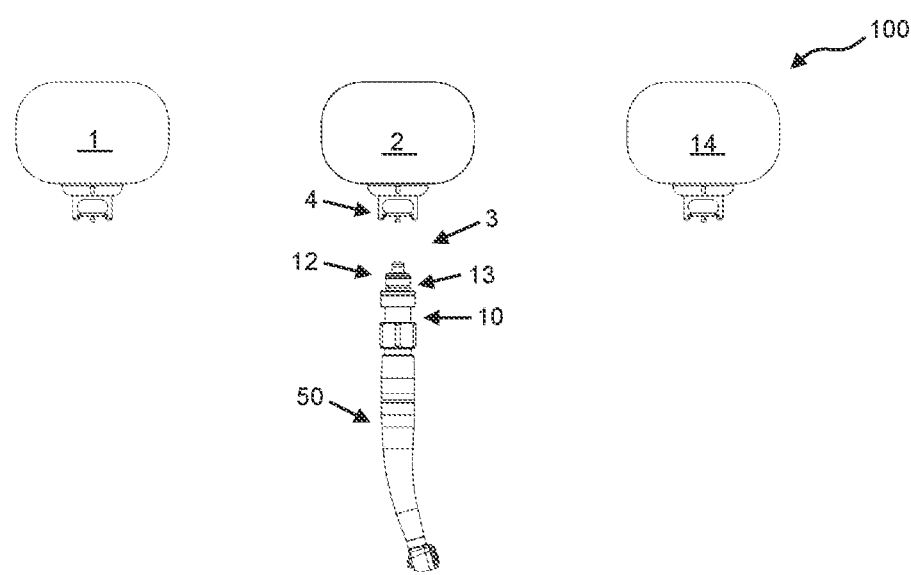

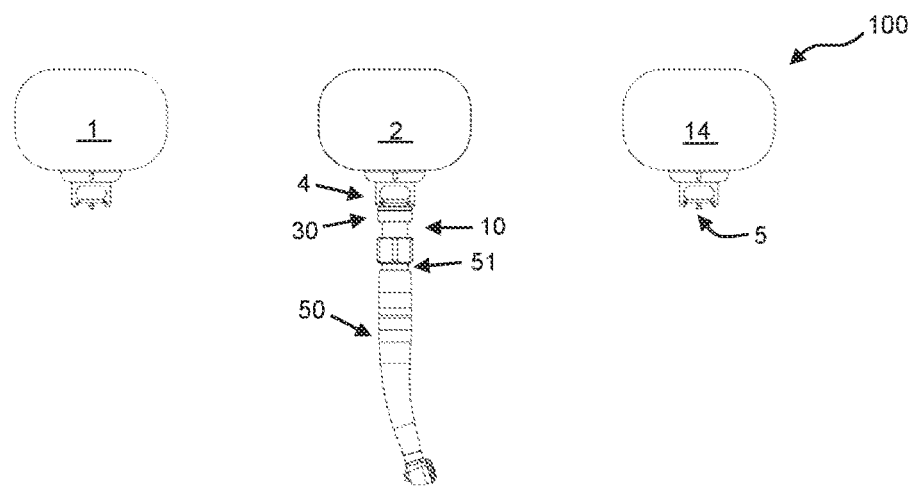
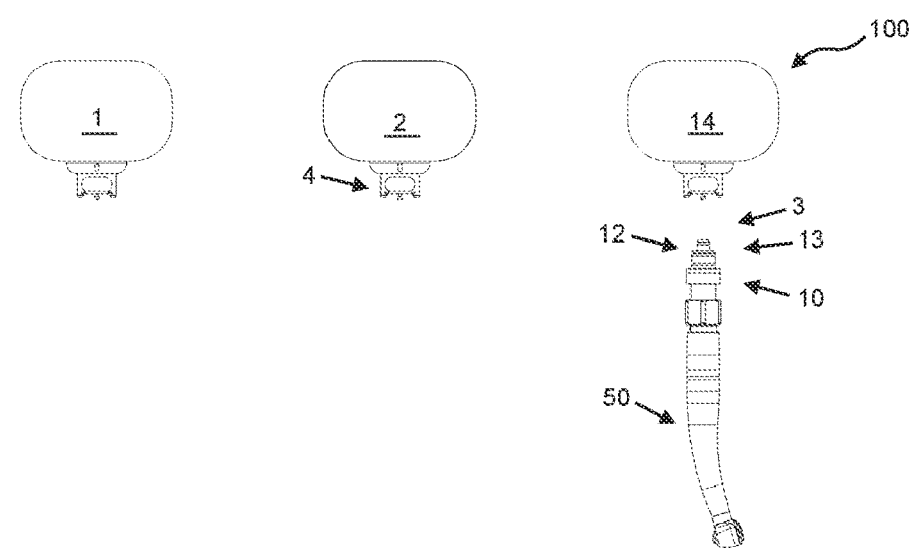
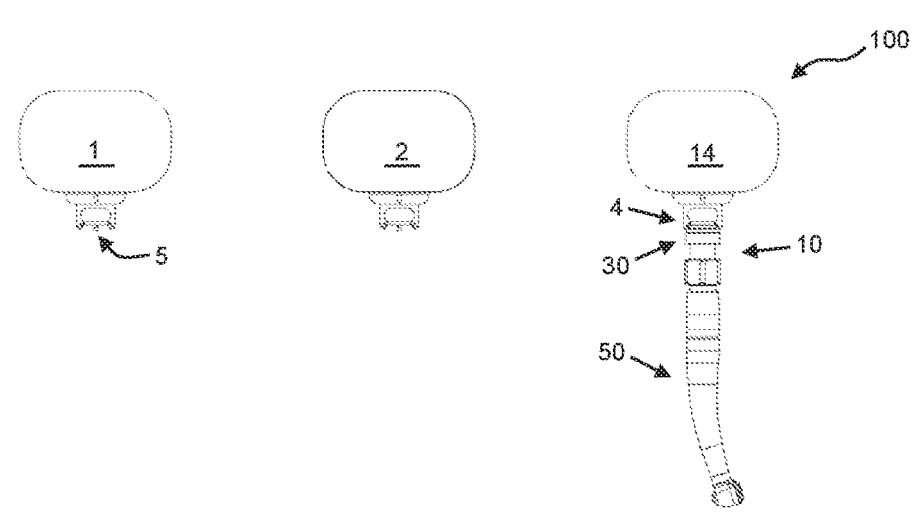

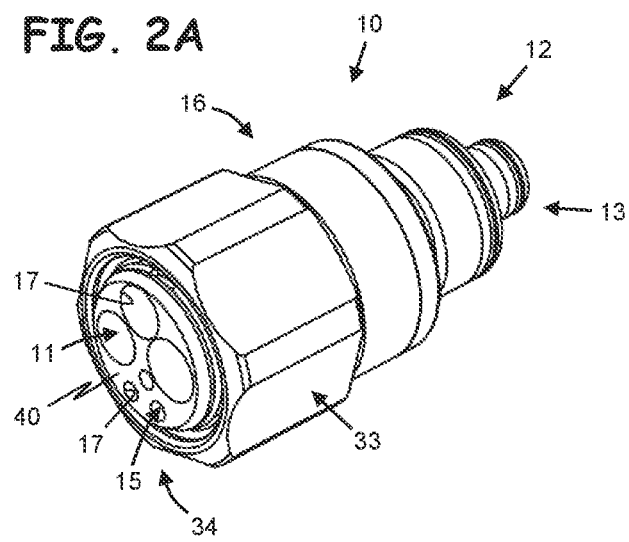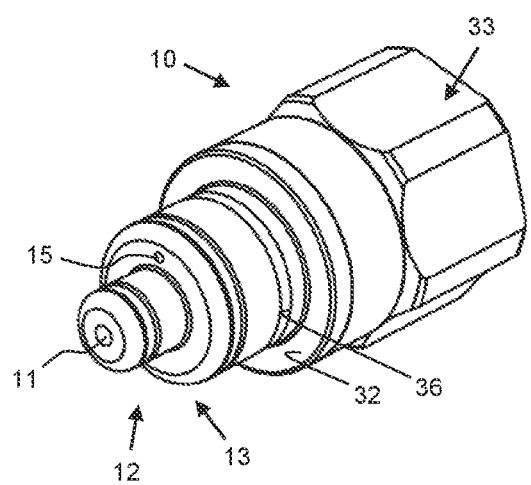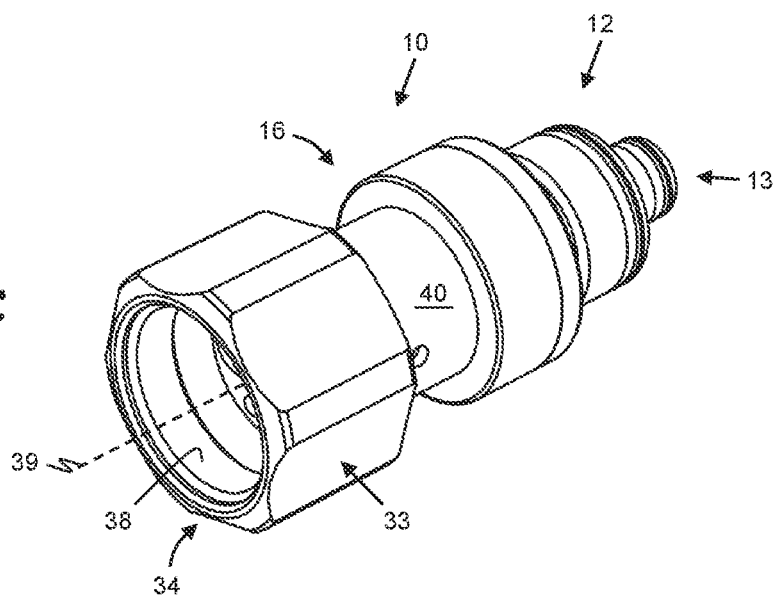

PREPARING AND/OR CARING FOR A MEDICAL OR DENTAL INSTRUMENT

CROSS REFERENCE TO RELATED APPLICATION

The present application claims priority from pending European Patent Application No. 20160298.4, filed Mar. 2, 2020, which is incorporated herein by reference.

FIELD

The present invention relates to a method and a system for preparing and/or caring for a medical or dental instrument.

DESCRIPTION OF PRIOR ART

According to current requirements, a treatment of a medical or dental instrument after its use comprises several steps, for example cleaning and/or disinfection, care and sterilisation. Often, these treatment steps are performed by different devices for preparation and/or care, and a user must remove and/or separate the medical or dental instrument from the corresponding device after each treatment step and place it in and/or connect it to a subsequent device.

Since the different devices for preparation and/or care and different medical or dental instruments often have different interfaces, it is necessary to provide a connection adapter to establish a connection between a device for preparation and/or care and a medical or dental instrument. Such connection adapters are particularly necessary when a preparation and/or care product is to be directed into the interior of a medical or dental instrument in order to prepare and/or care for the interior or components inside the medical or dental instrument. When changing from one device for preparation and/or care to another preparation and/or care device, a user must therefore also change the connection adapters in each case so that the medical or dental instrument can be connected to the following device for preparation and/or care.

SUMMARY

It is thus an object to make it easier for a user to carry out a method for preparing and/or caring for a medical or dental instrument and to shorten the time required for the preparation and/or care process in its entirety.

According to an embodiment there is provided a method, in particular a multi-step method for preparing and/or caring for a medical or dental instrument, comprising the following steps:
a) providing a connection adapter that is releasably connectable to a coupling end of the medical or dental instrument;
b) connecting, in particular releasably connecting, the medical or dental instrument via the connection adapter to a first preparation and/or care device for a medical or dental instrument;
c) preparing and/or caring for the medical or dental instrument by the first preparation and/or care device:
d) separating the connection adapter, together with the medical or dental instrument attached to it, from the first preparation and/or care device, the separation taking place in particular after completion of the preparation and/or care by the first preparation and/or care device;
e) connecting, in particular releasably connecting, the connection adapter, together with the medical or dental instrument attached thereto, to a second preparation and/or care device for a medical or dental instrument;
f) preparing and/or caring for the medical or dental instrument by the second preparation and/or care device.

Steps a) to f) are preferably performed sequentially and in particular in the order described, starting with step a) and ending with step f).

A connection adapter according to the invention is defined in that, in a method for preparing and/or caring for a medical or dental instrument, in particular in the method described above, the connection adapter can be releasably connected to a medical or dental instrument to be prepared and/or cared for, in particular to its coupling end, and selectively and/or at different times to a first and a second preparation and/or care device for a medical or dental instrument. The connection between the connection adapter, the instrument and the first or second preparation and/or care device comprises in particular a fluid-transferring connection.

A system for preparing and/or caring for a medical or dental instrument comprises: a first preparation and/or care device for a medical or dental instrument; a second preparation and/or care device for a medical or dental instrument; and a connection adapter which can be connected, with a medical or dental instrument to be prepared and/or cared for, in particular with its coupling end, to the first preparation and/or care device and the second preparation and/or care device, wherein the first preparation and/or care device and the second preparation and/or care device apply different preparation and/or care processes to the medical or dental instrument. In particular, the system is configured in such a way that it can be used to carry out a method for preparing and/or caring for a medical or dental instrument, in particular a method as defined above, in which the connection adapter and the medical or dental instrument attached thereto can be connected jointly (as a unit), selectively and/or at different times, to the first and second preparation and/or care device, so that at least one fluid or preparation and/or care medium can be transferred in a particularly preferred manner.

An advantage of the method for preparing and/or caring for a medical or dental instrument, the connection adapter, the system for preparing and/or caring for a medical or dental instrument, and the coupling device is that the connection adapter can be (operatively) connected to a plurality of preparation and/or care devices, so that the connection adapter and the medical or dental instrument attached thereto do not have to be separated during the method for preparation and/or care when changing from one preparation and/or care device to another preparation and/or care device and can thus be connected in particular as a (releasable) unit to at least two preparation and/or care devices used during a method. Preferably, the connection adapter or the connection adapter-instrument unit can be connected to all preparation and/or care devices of the method, so that no separation of the connection adapter-instrument unit is necessary during the entire preparation and/or care method. This simplifies the preparation and/or care method for the user and helps to save time. The number of connection adapters required is also advantageously reduced.

The connection of the medical or dental instrument to the connection adapter and/or the connection of the connection adapter to the first or second preparation and/or care device, as described for example in steps b) and e) of the above method, is caused in particular by the joining of plug-in connectors. The plug-in connectors are formed in particular by coupling elements or plug-in elements on the connection adapter, the instrument and the first and second preparation and/or care device, which are described in detail below. The separation of the medical or dental instrument from the connection adapter and/or the release of the connection adapter from the first or second preparation and/or care device, as described for example in step d) of the method, is also caused by the plug-in connectors.

Separating the connection adapter together with the medical or dental instrument secured to it from the first preparation and/or care device, as described for example in step d) of the above method, means in particular that the connection adapter and the instrument form a unit that is released from the first preparation and/or care device. In particular, the connection adapter and the medical or dental instrument are not released from each other. In particular, the connection adapter and the medical or dental instrument remain connected to each other during the separation from the first preparation and/or care device in the same way as they are connected during the previously occurring preparation and/or care by the first preparation and/or care device described, for example, in step c) of the above method. The connection adapter and the instrument are thus advantageously handled together, as a (unseparated) unit, during the method.

Connecting the connection adapter, together with the medical or dental instrument attached thereto, to or on the second preparation and/or care device, as described for example in step e) of the above method, means in particular that the connection adapter and the instrument form a unit which is secured to the second preparation and/or care device. In particular, the connection adapter and the medical or dental instrument are thereby not released from each other in this process. In particular, the connection adapter and the medical or dental instrument, when connected to the second preparation and/or care device, remain connected to each other as they are connected during the previously occurring preparation and/or care by the first preparation and/or care device, such as described in step c) of the above method, and/or when separated from the first preparation and/or care device, such as described in step d) of the above method. The connection adapter and the instrument are thus advantageously handled together, as a (unseparated) unit, during the method.

Preferably, connecting the medical or dental instrument via the connection adapter to the first preparation and/or care device, as described for example in step b) of the above method, comprises the following sub-steps:
  b1) (releasably) connecting the medical or dental instrument, in particular the coupling end of the instrument, to the connection adapter,
  b2) (releasably) connecting the connection adapter, together with the medical or dental instrument secured thereto, to the first preparation and/or care device, in particular to a coupling piece of the first preparation and/or care device.

Preferably, step b1) is carried out first and then step b2), which makes handling particularly easy for the user. Alternatively, it is also possible to first (releasably) secure the connection adapter to the first preparation and/or care device, in particular to a coupling piece of the first preparation and/or care device, and then (releasably) connect the medical or dental instrument, in particular its coupling end, to the connection adapter.

By connecting the connection adapter and the instrument, as described for example in step b1), the connection adapter and the instrument thus form a unit that is used in a plurality of different preparation and/or care devices or steps of a method for preparation and/or care without being (temporarily) separated. The connection adapter and the instrument are thus advantageously handled together, as a (unseparated) unit, during the (entire) method, in particular when connecting to the first preparation and/or care device, for example in step b2) of the above method, and particularly preferably also during the preparation and/or care, for example in steps c) and f) of the above method, when separating the connection adapter with the instrument from the first preparation and/or care device, for example in step d) of the above method, and when connecting the connection adapter with the instrument to the second preparation and/or care device, for example in step e) of the above method. In particular, the connection adapter and the medical or dental instrument, during one or more subsequent steps of the preparation and/or care method and/or when switching between different preparation and/or care devices, remain connected to each other as they were connected to each other in one or more previous steps of the preparation and/or care method or in a previously used preparation and/or care device.

Preferably, at or after the end of the method for preparation and/or care, in particular after completion of the last preparation and/or care step of the medical or dental instrument, for example after step f) of the above method, the medical or dental instrument is separated from the connection adapter.

Preferably, the connection adapter together with the medical or dental instrument secured to it is first separated from the last used, for example second preparation and/or care device according to the above method. Then, the medical or dental instrument is released from the connection adapter, in particular the unit of the connection adapter and the instrument described above is separated. This sequence is particularly easy for a user to handle.

Alternatively, it is also possible to separate the medical or dental instrument from the connection adapter first, so that the connection adapter still remains on the last used, for example second preparation and/or care device. The connection adapter is then separated (without the instrument) from the second preparation and/or care device.

Preferably, the medical or dental instrument comprises a hollow outer sleeve in which at least one component is arranged, wherein the preparation and/or care of the medical or dental instrument by the first preparation and/or care device and/or by the second preparation and/or care device comprises a preparation and/or care of the at least one component arranged inside the hollow outer sleeve. In particular, the preparation and/or care of the interior of the outer sleeve comprises directing a preparation and/or care medium towards or to the at least one component. For example, the at least one component inside the outer sleeve comprises at least one of the following components: an air line; a water line; a media line; a fluid line, a gear; a transmission; a bearing for a movable component of the medical or dental instrument; a tool holder; a tool release device; and similar components.

The medical or dental instrument is connected by the connection adapter in particular to a coupling piece of the first or second preparation and/or care device. The coupling piece is configured in particular as a plug-in element or as part of the plug-in connector for connection to the connection adapter, as already described above. The coupling piece preferably comprises at least one media line for conducting a preparation and/or care medium, wherein the media line ends in particular in an opening on a surface of the coupling piece, for example on a surface of a coupling receptacle of the coupling piece.

Preferably, the coupling piece of the first and/or second preparation and/or care device is configured in such a way that it directs a preparation and/or care medium into the interior of the hollow outer sleeve of the medical or dental instrument to be prepared and/or cared for, in particular into or towards at least one component in the hollow outer sleeve, as already described above. Advantageously, this makes it possible to clean or prepare the interior of the instrument. Preferably, the coupling piece is shaped in such a way that it can be received in the hollow outer sleeve of the medical or dental instrument.

The coupling piece comprises, for example, a bore arranged such that, when the coupling piece is connected to the instrument, a preparation and/or care medium flows into the interior of the hollow outer sleeve, in particular into or towards the at least one component. Particularly preferably, the bore is arranged on the coupling piece such that, when the coupling piece is connected to the instrument, the bore is received in the hollow outer sleeve. Alternatively or additionally, the coupling piece comprises, for example, a bore which, when the instrument is secured to the coupling piece, is connected to a media line of the medical or dental instrument for conducting a preparation and/or care medium into the media line.

The at least one media line of the coupling piece is preferably connected to a media source which provides and/or stores the preparation and/or care medium. The at least one media line of the coupling piece preferably extends from the coupling piece through the first or second preparation and/or care device to the media source or the at least one media line of the coupling piece is connected to the media source via a supply line. The media source can, for example, comprise a container for the preparation and/or care medium and/or a connection to a media supply, in particular a water supply, an evaporator or a compressor.

In order for the connection adapter to be connectable to the coupling piece of the first and second preparation and/or care device, so that in particular a method described above for preparation and/or care can be carried out, the coupling pieces of the first and second preparation and/or care device are configured identically or substantially identically. Alternatively, the coupling pieces of the first and second preparation and/or care devices differ (slightly) from each other, although, despite the differences, the connection adapter can be connected to both coupling pieces in a functional manner, in particular in a fluid-transferring manner, so that, in particular, a preparation and/or care medium can be passed through the at least one media line of the connection adapter from the first preparation and/or care device to the medical or dental instrument, in particular into its interior, and from the second preparation and/or care device to the medical or dental instrument, in particular into its interior. For example, the coupling pieces of the first and the second preparation and/or care device differ with respect to one or more of the mentioned characteristics: dimension; shape; design; connection interface; material; and similar properties.

The preparation and/or care medium may comprise, for example, at least one of the following media or combinations thereof: a preparation or cleaning medium, in particular a cleaning liquid or a rinsing agent, for example a detergent, a surfactant or a pressurised gas; a disinfection medium, in particular a disinfection liquid or a disinfection gas, for example an oxidising agent, an organic agent or an agent containing metal ions; a sterilisation medium, in particular a gaseous medium such as steam; a care medium, for example a lubricant, in particular based on plant substances and/or mineral oil, or a gaseous medium, for example for blowing through the instrument.

The preparation and/or care of a medical or dental instrument according to the method comprises at least two of the following treatments or combinations thereof: a care, in particular with a care medium described above; a preparation or cleaning, in particular with a preparation or cleaning medium described above; a disinfection, in particular with a disinfection medium described above; a sterilisation, in particular with a sterilisation medium described above. The at least two treatments are carried out in particular in a staggered or successive manner.

At least two treatments (or treatment steps) of the method for the preparation and/or care of a medical or dental instrument are carried out by two different preparation and/or care devices, for example by a first preparation and/or care device and a second preparation and/or care device, wherein, in order to carry out the method and/or the at least two treatments, it is necessary to connect the medical or dental instrument to be prepared and/or cared for (at staggered times) to the first preparation and/or care device and the second preparation and/or care device. The two different preparation and/or care devices are preferably two devices which are independent of each other and/or separate from each other, in particular spatially separate from each other. However, it is also conceivable that the first and second preparation and/or care devices form a combined apparatus with a common housing.

The two different preparation and/or care devices preferably comprise separate media sources and/or media supplies of operating media and/or preparation and/or care media. The two different preparation and/or care devices comprise, in particular, (spatially) separate chambers for receiving the medical or dental instrument to be prepared and/or cared for, each with at least one coupling piece for connecting the instrument, so that, in order to carry out the method and/or the at least two treatments, it is necessary to introduce the instrument (at staggered times) into the chamber of the first preparation and/or care device and the second preparation and/or care device and, in particular, to connect the instrument to the coupling piece of the chamber in question.

According to the method, the different preparation and/or care devices comprise at least two of the following devices or combinations thereof: a care device which in particular delivers a care medium, preferably as described above, to the medical or dental instrument; a preparation or cleaning device which in particular delivers a preparation or cleaning medium, preferably as described above, to the medical or dental instrument; a disinfection device which in particular delivers a disinfection medium, preferably as described above, to the medical or dental instrument; a steriliser or autoclave which delivers a sterilisation medium, preferably as described above, to the medical or dental instrument.

In particular, according to the method or during the at least two different treatment steps of the method the first and second preparation and/or care device supply the medical or dental instrument to be prepared and/or cared for with at least one different preparation and/or care medium. In particular, the first and second preparation and/or care device subject the instrument to different treatments, as described in particular above, whereby a comprehensive preparation and/or care of the medical or dental instrument is advantageously achieved.

The medical or dental instrument comprises in particular hollow instruments, for example instruments with a hollow outer sleeve, in the interior of which at least one component is arranged. Preferably, the interior of the medical or dental instrument and/or the at least one component is to be prepared and/or cared for by the first and/or second preparation and/or care device. The medical or dental instrument comprises, for example, a straight, curved or angled handpiece or contra-angle handpiece or an endoscopic instrument.

The medical or dental instrument comprises in particular a coupling end which is provided for connection to the first and second preparation and/or care device. The coupling end is preferably formed as a coupling receptacle, for example a coupling tube, for receiving a coupling extension. Alternatively, the coupling end may have one or more extensions, for example at least a portion of a media line extending through the instrument and/or an electrical contact extending particularly from the coupling end. Alternatively, the coupling end of the medical or dental instrument may be formed by a rotary coupling releasably connected to the instrument such that the instrument is rotatable relative to the rotary coupling. The end of the rotary coupling remote from the instrument is preferably provided with one or more extensions, for example at least a portion of a media line and/or an electrical contact extending through the instrument, particularly extending from the end of the rotary coupling.

The coupling end of the instrument, for example the coupling receptacle or at least one of the extensions, has at least one opening through which a preparation and/or care medium can be conducted into the interior of the instrument, in particular into the interior of a hollow outer sleeve and/or to a component arranged in the outer sleeve and/or into a media line of the medical or dental instrument, so that the interior of the instrument can also be prepared and/or cared for in an advantageous manner. The coupling end may, for example, have a thread, in particular an external thread, for connection to the connection adapter. The coupling receptacle can, for example, be configured as part of a plug-in connector or as a plug-in receptacle for a frictionally engaged and/or positive connection to the connection adapter, as already mentioned above.

The connection adapter comprises at least one media line for a preparation and/or care medium, in particular for passing through a preparation and/or care medium. Preferably, the at least one media line extends through the connection adapter, in particular along a longitudinal axis of the connection adapter, whereby a reliable transmission of the medium is advantageously achieved. Preferably, the at least one media line connects a first opening on a surface of the connection adapter to a second opening on a surface of the connection adapter, wherein the first and second openings are spaced apart from each other, in particular arranged at opposite ends of the connection adapter.

Preferably, the connection adapter, in particular the at least one media line, is provided for conducting a preparation and/or care medium from the first preparation and/or care device, in particular from its coupling piece, or from the second preparation and/or care device, in particular from its coupling piece, to the medical or dental instrument. Particularly preferably, the connection adapter, in particular the at least one media line, is intended to conduct a preparation and/or care medium into the hollow outer sleeve of the medical or dental instrument connected to the first or second preparation and/or care device, preferably to at least one component in the hollow outer sleeve, so that the interior of the instrument can also be prepared and/or cared for in an advantageous manner.

Particularly preferably, the connection adapter is configured in such a way that, by coupling the connection adapter to the medical or dental instrument and the first or second preparation and/or care device, a fluid connection for conducting the preparation and/or care medium can be established between the first or second preparation and/or care device, in particular its coupling piece, and the instrument to be prepared and/or cared for. Particularly preferably, the coupling of the connection adapter to the medical or dental instrument and the first or second preparation and/or care device establishes a fluid connection between the at least one medium line of the connection adapter, the at least one medium line of the first or second preparation and/or care device, in particular its coupling pieces, and the instrument, in particular the interior of the instrument. Particularly preferably, the openings of the various media lines of the connection adapter, the first or second preparation and/or care device and the instrument are fluidically connected to each other to establish the fluid connection, whereby a reliable media transfer is achieved in an advantageous manner.

Preferably, the connection adapter comprises a body extending along a longitudinal axis. Preferably, the at least one media line is arranged in and/or extends through the body, thereby advantageously ensuring reliable media transmission.

Preferably, the connection adapter comprises a plurality of media lines, for example two media lines, extending through the body of the connection adapter, so that a plurality of media can be advantageously transmitted. Preferably, one of the plurality of media lines is provided for conducting a care medium and another of the two media lines is provided for conducting a preparation medium, thereby advantageously avoiding mixing of different media. Preferably, an opening of one of the plurality of media lines is arranged centrically (in relation to the longitudinal axis of the connection adapter), whereby a particularly simple transfer of media is possible in an advantageous manner, independently of the rotational position of the connection adapter. Preferably, the centrally arranged opening is provided at the end of the connection adapter that is intended for connection to the first or second preparation and/or care device. Preferably, an opening of one of the plurality of media lines is arranged eccentrically or radially offset (with respect to the longitudinal axis of the connection adapter).

Preferably, openings of different media lines arranged at the same end of the connection adapter, for example at the end of the connection adapter for connection to the first or second preparation and/or care device or at the end of the connection adapter for connection to the medical or dental instrument, are provided on different surfaces of the connection adapter. The different surfaces are, for example, axially offset (with respect to the longitudinal axis of the connection adapter) and/or are formed by annular shoulders with different radii (from the longitudinal axis of the connection adapter). In this way, a reliable transfer of media is advantageously achieved, in which, for example, different media do not come into contact with each other.

Preferably, a connection element is provided on the connection adapter for connecting a medical or dental instrument to be prepared and/or cared for. Preferably, the connection element is provided at an instrument-side end of the connection adapter.

Preferably, the connection element comprises a plug-in element or part of a plug-in connector, whereby a quick and easy connection of the connection adapter to the instrument is advantageously achievable. Preferably, the connection element or the plug-in element comprises one or more openings or blind bores for receiving plug-in elements of the medical or dental instrument, for example line sections or electrical contacts protruding from the coupling end of the instrument.

Preferably, the at least one media line of the connection adapter extends through the connection element. Preferably, the at least one media line of the connection adapter ends at the connection element, in particular at a free end or at a surface of the connection element, and/or the opening of the at least one media line is arranged there, whereby a simple and safe media transfer is advantageously formed at the interface between the connection adapter and the instrument.

Preferably, the connection element comprises a cylindrical tube, which in particular forms part of the plug-in connector at the interface between the connection adapter and the medical or dental instrument. Preferably, the at least one media line of the connection adapter extends through the cylindrical tube. Preferably, the at least one media line of the connection adapter terminates at the cylindrical tube, in particular at a free end or at a surface of the cylindrical tube, and/or the opening of the at least one media line is arranged there, whereby a reliable media transfer is advantageously formed at the interface between the connection adapter and the instrument.

Particularly preferably, the connection element comprises a union nut with an internal thread for screw connection to a thread, in particular an external thread, of the medical or dental instrument. Preferably, the union nut is rotatably arranged on the connection adapter, in particular on its instrument-side end, especially preferably on the cylindrical tube. Preferably, the union nut secures the plug-in connection between the connection adapter and the medical or dental instrument, so that an unintentional separation of the connection adapter from the instrument is prevented in an advantageous manner.

Preferably, the union nut is slidable along a longitudinal axis of the connection adapter and/or the connection element and/or the cylindrical tube, which advantageously facilitates the connection of the connection adapter to the medical or dental instrument. Preferably, the cylindrical tube is at least partially received in the union nut. Preferably, the union nut surrounds at least part of the cylindrical tube. Preferably, the union nut is slidably and rotatably arranged on the cylindrical tube.

Preferably, the connection element, in particular the cylindrical tube, comprises a movable projection, for example a lug, for engagement with a recess on the medical or dental instrument. Preferably, the projection secures the plug-in connection of the connection adapter to the instrument so as to advantageously prevent inadvertent separation of the connection adapter from the instrument. Preferably, the extension is radially movable (with respect to the longitudinal axis of the connection adapter). Preferably, the extension is pretensioned by a spring element. Preferably, the extension is connected to an operating element for a user, for example a lever, in particular to move the extension radially in order to be able to establish and/or separate the connection between the connection adapter and the instrument.

Preferably, a coupling element is provided on the connection adapter for (releasable) connection of the connection adapter to one or more preparation and/or care devices, in particular to the first and second preparation and/or care devices described above.

Preferably, a coupling piece is provided on at least one preparation and/or care device, in particular on the first and second preparation and/or care devices described above, for (releasable) connection to a connection adapter, in particular described above, to which a medical or dental instrument to be prepared and/or cared for can be connected, so that a fluid-transferring, in particular preparation and/or care medium-transferring, connection can be established between the at least one preparation and/or care device and the connection adapter and in particular a medical or dental instrument connected thereto. In particular, the coupling piece comprises a coupling piece of the first or second preparation and/or care device described above. In particular, the coupling piece is part of a plug-in connector or is configured as a plug-in element, as described above.

The coupling element of the connection adapter and the coupling piece of the at least one preparation and/or care device preferably form a coupling device, in particular a plug-in connection, which has already been described above. One of the two components, namely the coupling piece or the coupling element, comprises a coupling extension and the other of the two components, namely the coupling piece or the coupling element, comprises a coupling receptacle for plug-in reception of the coupling extension.

That of the two components (coupling piece or coupling element) which has the coupling receptacle, preferably the coupling piece of the at least one preparation and/or care device, comprises:
- a, preferably cylindrical, body in which the coupling receptacle is formed;
- at least one media line for conducting a preparation and/or care medium through the body, the media line terminating in an opening on a surface of the coupling receptacle;
- a locking plate movably arranged in the body, wherein the locking plate is selectively movable into a locking position and an unlocked position;
- a through-opening arranged in the locking plate, the through-opening being fluidly connected to the opening of the medium line and/or preferably to the coupling receptacle for the passage of the preparation and/or care medium;
- a first pretensioning element for pretensioning the locking plate,
- a locking pin slidably received in a bore of the body and having a locking piece and an unlocking piece;
- a locking opening in the locking plate through which the locking pin extends, the locking opening having a locking portion and an unlocking portion;
- a second pretensioning element for pretensioning the locking pin such that a contact end of the locking pin protrudes beyond the locking plate.

In the following, the interaction of said parts of the component with the coupling receptacle, preferably the coupling piece of the at least one preparation and/or care device, is described, with the locking plate being initially in its unlocked position. This serves exclusively to illustrate the operating principle and does not constitute a limitation of the subject of the invention.

By applying a force to or on the contact end of the locking pin, the contact end can be moved in the direction of the bore of the body against the pretension of the second pretensioning element. The action of the force and/or the movement moves or displaces the locking pin in particular further in the direction of the bore and preferably at least a piece of the locking pin into the bore. As a result of the movement, the locking piece of the locking pin is (automatically) received in the locking section of the locking opening, whereby the locking plate is movable (from the unlocked position) into the locking position due to the pretensioning force of the first pretensioning element and is fixed in the locking position. The force effect at or on the contact end is generated in particular by inserting or pushing the coupling extension into the coupling receptacle, in particular by contact of the coupling extension or a part thereof with the contact end.

By applying a force to the locking plate against the pretension of the first pretensioning element, the locking plate moves or displaces and again assumes the unlocked position, whereby due to the pretensioning force of the second pretensioning element, the contact end of the locking pin is (automatically) movable away from the bore of the body or moves away, preferably when the coupling receiver and the coupling extension and/or the coupling piece and the coupling element are or will be separated from each other, so that the contact end has sufficient space to move away from the bore of the body and/or to assume the unlocked position. In particular, the locking pin moves away from the bore and preferably at least a piece of the locking pin moves out of the bore. By this movement of the locking pin, the locking piece of the locking pin leaves the locking portion of the locking opening and the unlocking piece of the locking pin is or is again received in the unlocking portion of the locking opening. By receiving the unlocking piece in the unlocking section, the locking plate is fixed in the unlocked position.

Preferably, two or more media lines are provided in the body for conducting a preparation and/or care medium through the body. Preferably, each media line terminates in a (dedicated) opening on a surface of the coupling receptacle. Preferably, each opening for transferring a preparation and/or care medium is provided between the connection adapter, in particular its coupling element, and the at least one preparation and/or care device, in particular its coupling piece. With these designs, a separate transfer of the media is possible in an advantageous manner.

Preferably, openings of different media lines located at the same end of the coupling receptacle, preferably at the same end of the coupling piece of the at least one preparation and/or care device, are provided on different surfaces of the coupling receptacle. The different surfaces are, for example, arranged axially offset (with respect to the longitudinal axis of the coupling receptacle) and/or formed by annular shoulders with different radii (from the longitudinal axis of the coupling receptacle). In this way, a reliable transfer of media is advantageously achieved in which different media do not come into contact with each other.

Preferably, the at least one opening or one of the plurality of openings of the plurality of media lines is arranged centrally (with respect to the longitudinal axis of the coupling receptacle), which advantageously enables a particularly simple transfer of media independent of the rotational position of the coupling receptacle. Preferably, the centrally arranged opening can be arranged opposite a centrally arranged opening of the coupling extension and/or the connection adapter (when the coupling extension and the coupling receptacle are connected to each other).

Preferably, the at least one opening or one of the plurality of openings of the plurality of media lines is eccentrically or radially offset (with respect to the longitudinal axis of the coupling receptacle).

Preferably, the locking plate and/or the through-opening is movable or displaceable transversely or orthogonally to the at least one media line in the body and/or to the longitudinal axis of the coupling receptacle. Preferably, the locking plate is formed as an elongate and/or substantially rectangular plate.

Preferably, a groove is provided in the body, in which the locking plate and/or the through-opening is movably or displaceably received and in particular guided. Preferably, the edges of the locking plate are received in the groove, in particular in guides of the groove. Preferably, the groove is configured and/or the locking plate is accommodated therein in such a way that the through-opening is freely accessible, in particular for inserting the coupling extension. Preferably, the groove is arranged transversely or orthogonally to the at least one media line in the body and/or to the longitudinal axis of the coupling receptacle. Preferably, the groove is provided at an end of the coupling receptacle, in particular at an end facing the coupling extension (when the coupling extension and the coupling receptacle are connected to each other). This ensures reliable movement and guidance of the locking plate and/or the through-opening.

The locking plate and/or in particular the through-opening are selectively movable into a locking position and an unlocked position. In the locking position, the coupling receptacle and the coupling extension and/or the coupling piece and the coupling element and/or the connection adapter and the preparation and/or care device are connected to each other, in particular in a fluid- or preparation and/or care medium-transferring manner. In the locking position, the coupling receptacle and the coupling extension preferably engage in one another, in particular the coupling extension is received in the coupling receptacle.

In the unlocked position, the coupling receptacle and the coupling extension and/or the coupling piece and the coupling element and/or the connection adapter and the preparation and/or care device are separated or separable from each other. In the unlocked position, the coupling receptacle and the coupling extension preferably do not engage with each other, in particular the coupling extension is not received in the coupling receptacle.

Preferably, the through-opening arranged in the locking plate is dimensioned in such a way that at least a part of the coupling extension can be accommodated therein and/or can project through. Preferably, the through-opening is bounded by a peripheral edge or defines the peripheral edge in the locking plate. The peripheral edge is adapted to engage a recess on the coupling extension when the coupling extension is inserted into the coupling receptacle and the locking plate is in the locking position, such that the coupling piece and the coupling element are secured to one another. This allows a reliable connection to be made between the coupling receptacle and the coupling extension.

The first pretensioning element for pretensioning the locking plate and the second pretensioning element for pretensioning the locking pin are preferably configured as spring elements, for example as coil springs, compression springs or tension springs.

The locking pin is preferably movable or displaceable transversely or orthogonally to the locking plate and/or substantially parallel to the at least one media line or to the longitudinal axis of the coupling receptacle, thereby advantageously enabling easy actuation of the locking pin.

The locking pin, which is slidably received in a bore of the body, in particular an elongate locking pin, comprises a locking piece, an unlocking piece and a contact end. The outer diameter of the locking piece is in particular smaller than the outer diameter of the unlocking piece. The contact end is preferably arranged at a (free) end of the locking pin and/or forms a free end of the locking pin. In particular, the contact end comprises a flat contact surface. The locking piece, the unlocking piece and the contact end are preferably arranged axially (with respect to a longitudinal axis of the contact pin). Particularly preferably, the locking piece is arranged between the unlocking piece and the contact end. This design of the locking pin ensures a reliable function of the coupling device.

A locking opening is provided in the locking plate through which the locking pin extends. At least the contact end of the locking pin, preferably also at least a part of the locking piece, protrudes beyond the locking plate, so that in particular the contact end is freely accessible (for a force-exerting element), whereby in an advantageous manner a simple actuation of the locking pin is possible, in particular by contact through the coupling extension, as already described above.

The locking opening preferably has an elongate shape and/or slot shape. The locking opening is preferably arranged adjacent to the through-opening. The locking opening is preferably arranged in the same plane as the through-opening. The locking opening is separated from the through-opening, for example, by a section of the locking plate, in particular a web-like section. Alternatively, the locking opening opens into the through-opening, so that the locking opening forms in particular a slot-shaped extension of the through-opening. This design of the locking opening ensures reliable functioning of the coupling device.

The locking opening has a locking section, in particular for receiving the locking piece of the locking pin, and an unlocking section, in particular for receiving the unlocking piece of the locking pin. Preferably, the inner diameter of the locking portion is smaller than the inner diameter of the unlocking portion. Preferably, the unlocking portion is located closer to the through-opening and the locking portion is located further away from the through-opening. This design of the locking opening ensures reliable interaction with the locking pin.

Preferably, an actuator is provided on the locking plate, which advantageously facilitates the actuation of the locking plate for the user, in particular when it is moved from the locking position to the unlocked position. Preferably, the actuating element is arranged substantially opposite the locking opening. Preferably, the actuating element is a part of the locking plate, in particular an integral or one-piece part of the locking plate. Alternatively or additionally, the actuating element is preferably plate-shaped. Alternatively or additionally, the actuator is preferably arranged at an angle to the section of the locking plate in which the through-opening and/or the locking opening are located, in particular at an angle of approximately 90°. Alternatively or additionally, the actuator is preferably arranged approximately parallel to the coupling receptacle.

The other of the two components (coupling piece or coupling element), preferably the coupling element of the connection adapter, comprises the coupling extension to be received in the coupling receptacle. The coupling extension is preferably cylindrically shaped. The coupling extension preferably has a plurality of sections with different outer diameters.

Preferably, at least one media line for conducting a preparation and/or care medium extends through the coupling extension. In particular, the at least one media line is connected to the media line of the connection adapter or is part of the media line of the connection adapter. Preferably, the at least one media line is connected to an opening on a surface of the coupling extension. Preferably, the opening is arranged centrally (with respect to the longitudinal axis of the coupling extension and/or the connection adapter), so that it is in particular in fluid communication with the central opening of the coupling receptacle, whereby a reliable media transfer is advantageously formed at the interface between the connection adapter and the preparation and/or care device.

Preferably, a recess is provided on the coupling extension into which the peripheral edge of the through-opening of the locking plate engages when the coupling extension is inserted into the coupling receptacle and the locking plate assumes the locking position, whereby the coupling piece and the coupling element are reliably secured to each other in an advantageous manner. The recess comprises, for example, a groove, an annular groove, a cut-out or similar elements. In order to be able to separate the coupling receiver and the coupling extension and/or the coupling piece and the coupling element from each other, the engagement of the peripheral edge in the recess must be terminated, which can be effected by displacing the locking plate against the spring force of the first pretensioning element, as already described above.

Preferably, a contact surface is provided on the coupling extension which is arranged in such a way that, when the coupling extension is inserted into the coupling receptacle, it exerts the force on the contact end of the locking pin by contact with the contact end, to move the contact end in the direction of the bore of the body against the pretension of the second pretensioning element until the locking piece of the locking pin is received in the locking section of the locking opening, whereby the locking plate is moved into the locking position due to the pretension of the first pretensioning element. Thus, in an advantageous manner, the locking between the coupling extension and the coupling receptacle is effected by pushing the coupling extension into the coupling receptacle, without any additional necessary manual action by the user. The contact surface comprises, for example, an annular surface, annular shoulder and/or a step on the coupling extension.

The coupling device described above may be used in a method for preparing and/or caring for a medical or dental instrument described above or in a system for preparing and/or caring for a medical or dental instrument described above. Alternatively, the coupling device is a separate invention that may be implemented in any other method for preparing and/or caring for a medical or dental instrument, preparation and/or care devices for medical or dental instruments, or systems for preparing and/or caring for a medical or dental instrument.

Preferably, a preparation and/or care device for preparing and/or caring for a medical or dental instrument is provided and has a coupling piece with a coupling receptacle described above. Particularly preferably, the preparation and/or care device comprises the coupling device described above and the connection adapter described above.

Preferably, the preparation and/or care device comprises at least one of the following devices: a care device which in particular delivers a care medium, preferably as described above, to the medical or dental instrument; a device for preparation or cleaning which in particular delivers a preparation or cleaning medium, preferably as described above, to the medical or dental instrument; a device for disinfection which in particular delivers a disinfection medium, preferably as described above, to the medical or dental instrument; a steriliser or autoclave which delivers a sterilisation medium, preferably as described above, to the medical or dental instrument.

Preferably, the preparation and/or care devices comprise at least one media source and/or media supply for operating media and/or preparation and/or care media. The two different preparation and/or care devices comprise, in particular, (spatially) separate chambers for receiving the medical or dental instrument to be prepared and/or cared for, each with at least one coupling piece for connecting the instrument, so that, in order to carry out the method and/or the at least two treatments, it is necessary to introduce the instrument (at staggered times) into the chamber of the first preparation and/or care device and the second preparation and/or care device and, in particular, to connect the instrument to the coupling piece of the chamber in question.

Furthermore, the preparation and/or care device may have one or more features of the preparation and/or care devices described above, and therefore reference is made to these features in order to avoid repetition.

These and other embodiments will be described below with reference to the following drawings.

BRIEF DESCRIPTION OF THE DRAWINGS

FIGS. 1A-1F show a system for preparing and/or caring for a medical or dental instrument and a step-by-step procedure of a method for preparing and/or caring for a medical or dental instrument with three different preparation and/or care devices, wherein a medical or dental instrument and a connection adapter releasably connected thereto are connected jointly and sequentially in time to each of the three different preparation and/or care devices, so that the medical or dental instrument can be prepared and/or cared for by the three preparation and/or care devices.

FIGS. 2A-2C show a connection adapter that is releasably connectable to a medical or dental instrument and that is intended to connect the medical or dental instrument to one or more preparation and/or care devices so that the medical or dental instrument can be prepared and/or cared for by the three preparation and/or care devices.

DETAILED DESCRIPTION

Figure 3A:
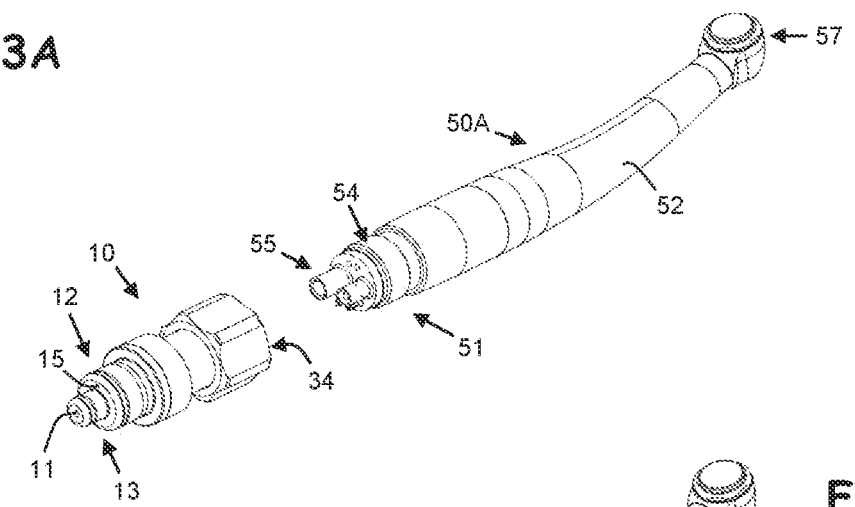
FIGS. 3A and 3B show a first medical or dental instrument and a connection adapter releasably connectable and connected thereto.

The system 100 for preparing and/or caring for a medical or dental instrument 50 shown in FIGS. 1A-1F comprises a plurality of, in this case three, different preparation and/or care devices 1, 2, 14 which apply different preparation and/or care processes to the instrument 50. For example, the preparation and/or care device 1 may comprise a device for cleaning and/or disinfection, in particular configured to treat the instrument 50 with a disinfectant and/or with a cleaning agent and/or with hot water; for example, the preparation and/or care device 2 may comprise device for care intended in particular to blow through the instrument 50 with a compressed gas (compressed air) and/or to supply it with a lubricant; for example, the preparation and/or care device 14 may comprise a steriliser or autoclave for delivering a sterilisation medium to the instrument 50.

It is expressly pointed out once again that the system 100 shown in FIGS. 1A-1F and the preparation and/or care devices 1, 2, 14 mentioned are exemplary. In particular, the number of the plurality of preparation and/or care devices 1, 2, 14 may vary. For example, it is also possible that the system 100 comprises only two preparation and/or care devices, preferably care device 2, which is in particular intended to blow through the instrument 50 with a compressed gas (compressed air) and/or to supply it with a lubricant, and a steriliser or autoclave 14 for delivering a sterilisation medium to the instrument 50. The devices that make up the system 100 can also vary, for example, a device that uses a different preparation and/or care medium than those mentioned or a different technology, for example ultrasound or radiation, such as UV radiation, to prepare and/or care for the instrument 50 can also be part of the system 100.

The preparation and/or care devices 1, 2, 14 shown schematically in FIGS. 1A-1F each comprise at least one coupling piece 4 with a coupling receptacle 5 for connecting the instrument 50 to be prepared and/or cared for. The coupling piece 4 is configured as part of a plug connector 3. The coupling piece 4 or the coupling receptacle 5 is in particular configured to transfer fluid, so that at least one preparation and/or care medium can be transferred to the medical or dental instrument 50 via the coupling piece 4. Particularly preferably, the coupling piece 4 has at least one fluid line which ends in an opening on a surface of the coupling piece 4 in such a way that the preparation and/or care medium which can be conveyed in the fluid line can be transferred into the interior of the instrument 50.

FIGS. 1A-1F also show a medical or dental instrument 50 to be prepared and/or cared for, which is configured here by way of example as a dental handpiece. A connection adapter 10 is releasably secured to the coupling end 51 of the instrument 50. For this purpose, the connection adapter 10 has a connection element 34 which can be connected to the coupling end 51 of the medical or dental instrument 50 or to a coupling end of a rotary coupling which is releasably connected to the instrument 50, in particular can be connected in a fluid-transferring manner, so that a preparation and/or care medium can be transferred into the interior of the instrument 50.

Furthermore, a coupling element 12 is provided on the connection adapter 10, in particular in the form of a coupling extension 13, which can be releasably connected to the coupling piece 4 of the preparation and/or care devices 1, 2, 14. The coupling element 12 and/or the coupling extension 13 form in particular a part of the plug connector 3, preferably the coupling extension 13 is insertable into the coupling piece 4. The connection between the coupling element 12 and the coupling piece 4 is preferably again fluid-transferring, so that a preparation and/or care medium can be transferred into the interior of the instrument 50.

The coupling pieces 4 of the preparation and/or care devices 1, 2, 14 are configured in such a way that the connection adapter 10 can be connected to each coupling piece 4 (functionally or operatively), in particular in such a way that at least one preparation and/or care medium can be transferred from a preparation and/or care device 1, 2, 14 via the connection adapter 10 into the interior of the instrument 50. Preferably, the coupling pieces 4 of the several preparation and/or care devices 1, 2, 14 are identical or substantially identical.

A method for preparing and/or caring for a medical or dental instrument 50, which can be carried out with the system 100, is thus defined by the fact that the instrument 50 and the connection adapter 10 connected thereto pass through the method jointly or as a unit, in particular as a unit temporarily formed for the method for preparation and/or care. In other words, the instrument 50 and the connection adapter 10 are connected as a unit to at least two preparation and/or care devices 1, 2, 14 and the instrument 50 is prepared or cared for by each preparation and/or care device 1, 2, 14 without the instrument 50 and the connection adapter 10 being separated from each other.

FIG. 1A shows the instrument 50 connected to the connection adapter 10 before the start of the first preparation and/or care by the preparation and/or care device 1. In FIG. 1B, the instrument 50 and the connection adapter 10 are connected to the first preparation and/or care device 1 so that the preparation and/or care, in particular also of the interior of the instrument 50, can begin or is in progress. After completion of the preparation and/or care by the preparation and/or care device 1, the instrument 50 and the connection adapter 10 are released jointly (as a unit) from the preparation and/or care device 1, see FIG. 1C, and are then connected together (as a unit) to the preparation and/or care device 2, see FIG. 1D and also FIG. 5. This is followed by preparation and/or care, in particular also of the interior of the instrument 50, by the preparation and/or care device 2, after the completion of which the instrument 50 and the connection adapter 10 are separated jointly (as a unit) from the preparation and/or care device 2, see FIG. 1E. Finally, the instrument 50 and the connection adapter 10 are connected jointly (as a unit) to the preparation and/or care device 14 of FIG. 1F in order to prepare and/or care for the instrument 50, in particular also its interior. After completion of the final preparation and/or care, the instrument 50, the connection adapter 10 and the preparation and/or care device 14 are separated from each other, preferably by first separating the instrument 50 and the connection adapter 10 jointly (as a unit) from the preparation and/or care device 14 and then removing the connection adapter 10 from the instrument 50.

In particular, FIGS. 2A-8 illustrate and describe a preferred embodiment of a connection adapter 10 and a coupling device 30 for connecting the connection adapter 10 to a preparation and/or care device 1, 2, 14. The connection adapter 10 and the coupling device 30 of FIGS. 2A-8 can be used in the system 100 and method described above for preparing and/or caring for a medical or dental instrument 50, which is certainly extremely advantageous due to the ease of handling for connecting and separating the connection adapter 10 and the coupling device 30. In principle, however, it is also possible to use any other coupling device and/or connection adapter for the system 100 and, in particular, the method for preparation and/or care with the system 100. Conversely, the connection adapter 10 and the coupling device 30 can be used with any preparation and/or care device which, in particular, is not part of a system 100 of a plurality of preparation and/or care devices and/or which is not used in a preparation and/or care method in which the instrument 50 to be prepared and/or cared for is connected jointly with the connection adapter 10, as a unit, to at least two preparation and/or care devices.

The connection adapter 10 shown in FIGS. 2A-2C comprises a body 16, in particular an elongate body, which extends along a longitudinal axis 39. At one end of the body 16, a connection element 34 is provided for releasably connecting a medical or dental instrument 50, 50A, 50B to be prepared and/or cared for. At an opposite end of the body 16, a coupling element 12 is provided for releasable connection to a coupling piece 4 of a preparation and/or care device 1, 2, 14.

For connection to the instrument 50, 50A, 50B, the connection element 34 is configured as a plug-in element or part of a plug-in connector. In particular, the connection element 34 comprises at least one or more openings 17 for receiving an extension 55 at the coupling end 51 of the instrument 50, 50A, 50B (see FIG. 3A) or at a rotary coupling 56 (see FIG. 3B), for example a section of a media line running through the instrument 50, 50A, 50B and/or an electrical contact.

A cylindrical tube 40 is provided on the connection element 34 or as part of the connection element 34. The at least one opening 17 is arranged on a free end surface of the cylindrical tube 40. A union nut 33 with an internal thread 38 is further provided on the connection element 34 or as part thereof for screw connection with an external thread 54 (see FIG. 3A) of the medical or dental instrument 50, 50A, 50B or the rotary coupling 56 (see FIG. 3B). The union nut 33 is rotatably arranged on the connection adapter 10, in particular on its cylindrical tube 40. After the connection adapter 10 has been plugged onto the instrument 50, 50 A, 50B via the at least one opening 17 and the at least one extension 55, the two threads 38, 54 are screwed together to secure this plug-in connection. In order to facilitate the connection of the connection adapter 10 to the medical or dental instrument 50, 50A, 50B, the union nut 33 is displaceable along the longitudinal axis 39 of the connection adapter 10 and/or along the cylindrical tube 40. Preferably, the axial length of the tube 40 is such that the union nut 33 is movable between a retracted position (towards the coupling element 12), in which in particular the free end of the tube 40 with the at least one opening 17 is not at all or only slightly recessed in the interior of the union nut 33 (see FIG. 2A), and an advanced position (further away from the coupling element 12), in which in particular the free end of the tube 40 with the at least one opening 17 is sunk deeper into the interior of the union nut 33, so that the screw connection of the two threads 38, 54 is possible (see FIG. 2C).

The coupling element 12 of the connection adapter 10 comprises a cylindrical coupling extension 13. The coupling extension 13 extends along the longitudinal axis 39 of the connection adapter 10. At least one seal, for example an O-ring received in a groove, is provided on the coupling element 12 or coupling extension 13.

The connection adapter 10 comprises at least one, according to FIGS. 2A-2C two, media lines 11, 15 for conducting at least one preparation and/or care medium from the preparation and/or care device 1, 2, 14 to and/or into the instrument 50, 50A, 50B. The at least one media line 11, 15 extends through the connection adapter 10 and connects a first opening at a surface of the connection adapter 10, for example at the free end of the cylindrical tube 40, to a second opening at a surface of the connection adapter 10, for example at the coupling element 12 or the coupling extension 13. The coupling of the medical or dental instrument 50, 50A, 50B with the preparation and/or care device 1, 2, 14 via the connection adapter 10 thus creates a fluid connection for conducting the preparation and/or care medium from the preparation and/or care device 1, 2, 14 to the instrument 50, 50A, 50B to be prepared and/or cared for.

In particular, FIG. 2B shows the contact surface 32 arranged on the coupling element 12 or coupling extension 13, which, when the coupling extension 13 is inserted into the coupling piece 4 or the coupling receptacle 5 of the preparation and/or care device 1, 2, 14, causes a locking between the coupling extension 13 and the coupling receptacle 5 by contact with a locking pin 22 of the coupling piece 4 (see FIG. 6) by pushing the coupling extension 13 into the coupling receptacle 5. The contact surface 32 comprises, for example, an annular surface, annular shoulder and/or a step on the coupling element 12.

FIG. 2B also shows the recess 36 arranged on the coupling element 12 or coupling extension 13, in which the peripheral edge 37 (see FIG. 8) of the locking plate 9 engages when the coupling extension 13 is inserted into the coupling receptacle 5, so that the coupling piece 4 of the preparation and/or care device 1, 2, 14 and the coupling element 12 are reliably secured to each other. The recess 36 comprises, for example, an annular groove or notch. In order to be able to separate the coupling piece 4 and the coupling element 12 from each other, the engagement of the peripheral edge 37 in the recess 36 must be terminated.

FIGS. 3A-4B show two different medical or dental instruments 50A, 50B and their connection to the connection adapter 10 of FIGS. 2A-2C.

Figure 3B:
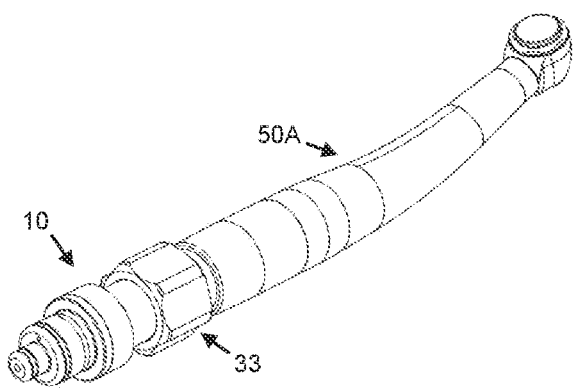

The instrument 50A of FIGS. 3A, 3B comprises a pneumatically operated handpiece. The handpiece known from the prior art comprises, inter alia, a pneumatically rotatable impeller, a tool holder connected to the impeller and rotatable by the impeller for releasably holding a treatment tool, at least one media line extending from the coupling end 51 through the hollow outer sleeve 52 towards, up to or into a head part 57 of the handpiece, and a so-called fixed connection at the coupling end 51 of the handpiece. In particular, the fixed connection comprises one or more extensions 55 extending from the coupling end 51 and the external thread 54. The at least one extension 55 comprises, for example, end portions of the media lines and/or electrical pin contacts extending through the instrument 50A. By the extensions 55 and the external thread 54, the instrument 50A can be coupled (non-rotatably) to a supply hose or to the connection adapter 10 (see FIG. 3B). This coupling creates the unit of the instrument 50, 50A, 50B and the connection adapter 10, which in the method described and illustrated in FIGS. 1A-1F for preparing and/or caring for a medical or dental instrument 50, 50A, 50B is connected successively to the plurality of preparation and/or care devices 1, 2, 14. This coupling of the instrument 50A and the connection adapter 10 in particular also creates the fluid-transferring connection between the preparation and/or care device 1, 2, 14 and the instrument 50A, which has already been described several times above.

Figure 4A:
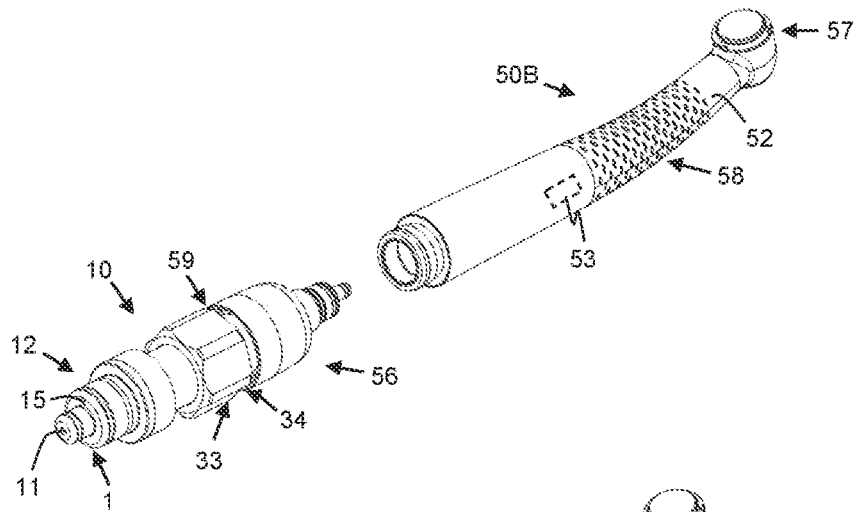
FIGS. 4A and 4B show a second medical or dental instrument having a rotary coupling and a connection adapter releasably connectable and connected thereto.
Figure 4B:
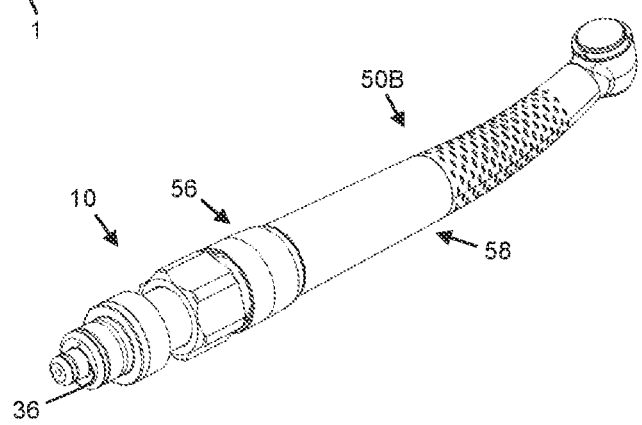

The instrument 50B of FIGS. 4A, 4B comprises a handpiece 58 and a rotary or swivel coupling 56 connectable to the handpiece 58, both of which are known in the prior art. The handpiece 58 comprises, inter alia, a rotatable tool holder disposed in the head portion for releasably holding a treatment tool and at least one media line extending through the hollow outer sleeve 52 towards, up to or into a head part 57 of the handpiece 58. The handpiece 58 also comprises a schematically illustrated component 53 disposed within the outer sleeve 52. The handpiece 58 is releasably and rotatably connectable to the swivel coupling 56 in a known manner. The rotary coupling 56 is penetrated by at least one media line for supplying the handpiece 58 with a medium and, where appropriate, by electrical conductors for supplying the handpiece 58 with electricity. The swivel coupling 56 is releasably connected to the connection adapter 10 via a coupling side 59, the coupling side 59 being of similar or identical construction to the coupling end 51 of the instrument 50A of FIG. 3A. In particular, the coupling side 59 comprises at least one projection 55 projecting from the coupling side 59 and receivable in an opening 17 of the connection adapter 19, and an external thread 54. The at least one projection 55 comprises, for example, end portions of the media lines extending through the rotary coupling 56 and/or electrical pin contacts of the electrical conductors. By the extensions 55 and the external thread 54, the rotary coupling 56 and the instrument 50B can be coupled to a supply hose or to the connection adapter 10 (see FIG. 4B). This coupling creates the unit of the instrument 50, 50A, 50B and the connection adapter 10, which in the method described and illustrated in FIGS. 1A-1F for the preparation and/or care of a medical or dental instrument 50, 50A, 50B is sequentially connected to the plurality of preparation and/or care devices 1, 2, 14. This coupling of the instrument 50B and the connection adapter 10 in particular also creates the fluid-transferring connection between the preparation and/or care device 1, 2, 14 and the instrument 50B, which has already been described several times above, and preferably thus also the preparation and/or care of the component 53 arranged inside the instrument 50B.

Figure 5:
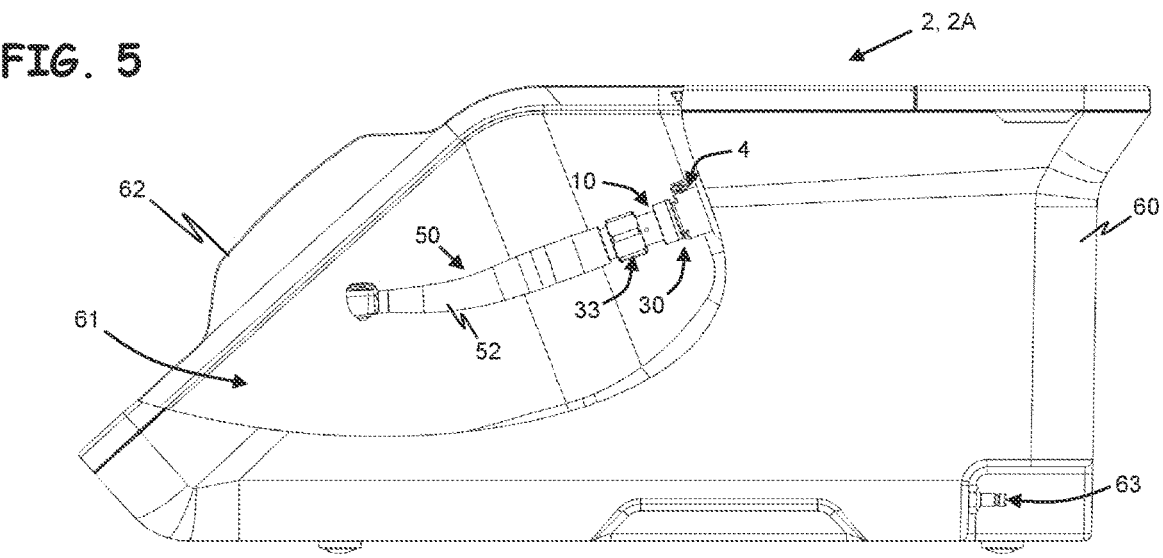
FIG. 5 shows an embodiment of a preparation and/or care device in the form of care device, in the care chamber of which a medical or dental instrument is received, which is releasably connected to a coupling piece of the care device by a connection adapter, so that a care medium can be transferred from the care device to the instrument.
Figure 6:
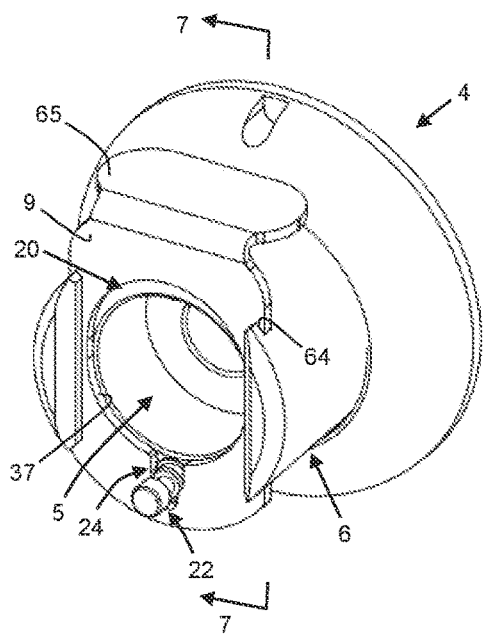
FIG. 6 shows an embodiment of a coupling piece of a preparation and/or care device, which is provided in particular for releasable connection to a medical or dental instrument by a connection adapter.

FIG. 5 shows a preparation and/or care device 2 in the form of care device 2A, which is intended in particular to blow through the instrument 50 with a compressed gas (compressed air) and to supply it with a lubricant. This prior-art care device 2A comprises, among other things, a housing 60 which forms a chamber 61 in which an instrument 50 to be prepared and/or cared for can be received. The chamber 61 is closable by a movable lid 62. The care device 2A further comprises at least one connection 63 to one or more external media sources, for example to a source of compressed air or a source of a preparation and/or care medium, and/or to an external power source. Inside the housing 60 there may be, for example, a container or a receptacle for a container for a preparation and/or care medium. Furthermore, inside the housing 60 there is provided a delivery device for at least one preparation and/or care medium, which has, for example, a pump, lines, valves and similar components and actuating elements, so that the at least one preparation and/or care medium can be delivered to the coupling piece 4 arranged in the chamber 61. Preferably, the care device 2A comprises an electrical control device or a controller for controlling the care device 2A, in particular the care process, and optionally a display and/or operating panel for a user, connected to the control device.

As can be seen in FIG. 5, an instrument 50 is connected to the coupling piece 4 by means of a connection adapter 10, in particular in a fluid-transferring manner, as is also shown schematically in FIG. 1D, for example. Thus, a preparation and/or care medium can be conveyed to or into the instrument 50. The design of the connection adapter 10 and the connection to the instrument 50 preferably correspond to the embodiments of FIGS. 2A-4B.

The coupling element 12 or the coupling extension 13 of the connection adapter 10 and the coupling piece 4 of the care device 2A form a coupling device 30 which, due to its construction, is particularly easy to handle and is therefore particularly advantageous to use in a method of preparation and/or care according to FIGS. 1A-1F. The coupling element 12, which forms the section of the coupling device 30 provided on the connection adapter 10, has already been described above, in particular in conjunction with FIGS. 2A-2C, so that in the following, with reference to FIGS. 6-8, mainly the structure of the coupling piece 4 and the interaction of the coupling element 12 and of the coupling piece 4 are described.

The coupling piece 4 has a, preferably cylindrical, body 6 in which the coupling receptacle 5 is formed, for example as a cylindrical bore. The coupling receptacle 5 projects at least a little into the body 6 so that the coupling extension 13 can be received therein.

A movable, in particular displaceable, locking plate 9 is provided on the body 6, which is selectively movable into a locking position and an unlocked position. A through-opening 20 is provided in the locking plate 9, the through-opening 20 being fluidically connected to the opening of a medium line 7 and/or to the coupling receptacle 5 for the passage of the preparation and/or care medium. The through-opening 20 is dimensioned in such a way that at least part of the coupling extension 13 of the coupling element 12 can be received therein.

A groove 64 is provided in the body 6, in which the locking plate 9 with the through-opening 20 is movably or displaceably received and in particular guided. For this purpose, the edges of the locking plate 9 are received in the groove 64, in particular in guides of the groove 64.

An actuator 65 is provided on the locking plate 9 or as a part thereof, whereby the actuation of the locking plate 9, in particular when it is moved from the locking position to the unlocked position, is facilitated for the user. The actuator 65 is planar and angled with respect to the portion of the locking plate 9 in which the through-opening 20 is located. A first pretensioning element 21, for example in the form of a coil spring, pretensions the locking plate 9, in particular into the locking position. The first pretensioning element 21 is preferably arranged between the body 6, for example in a receptacle of the body 6, and the actuator 65. The first pretensioning element 21 is provided in particular on an underside of the actuator 65 facing the body 6.

At least one media line 7 is provided on the coupling piece 4 for conducting a preparation and/or care medium through the body 6, the media line 7 extending through at least part of the body 6. The media line 7 ends in an opening 8 on a surface of the coupling receptacle 5 and/or is connected to the coupling receptacle 5 and the through-opening 20 fluidically.

A locking pin 22 is slidably received in a bore 23 of the body 6 arranged substantially at right angles to the locking plate 9. The locking pin 22 has a contact end 35, a locking piece 25 and an unlocking piece 26. The contact end 35 projects beyond the body 6 as a free end and can thus be contacted by a part of the coupling element 12 or the coupling extension 13, in particular by the contact surface 32. The locking pin 22 is pretensioned by a second pretensioning element 29, for example a coil spring, arranged in the bore 23, in particular into the unlocked position, in which the contact end 35 is further away from the body 6 than in the locking position. The outer diameter of the locking piece 25 is smaller than the outer diameter of the unlocking piece 26.

A locking opening 24 is provided in the locking plate 9 through which the locking pin 22 extends. The locking opening 24 has an elongate slot shape and opens into the through-opening 20. The locking opening 24 comprises a locking portion 27 for receiving the locking piece 25 of the locking pin 22, and an unlocking portion 28 for receiving the unlocking piece 26 of the locking pin 22. The inner diameter of the locking portion 27 is smaller than the inner diameter of the unlocking portion 28, in particular in the plane in which the locking plate 9 extends. The unlocking portion 28 is arranged closer to the through-opening 20 than the locking portion 27.

Figure 7:
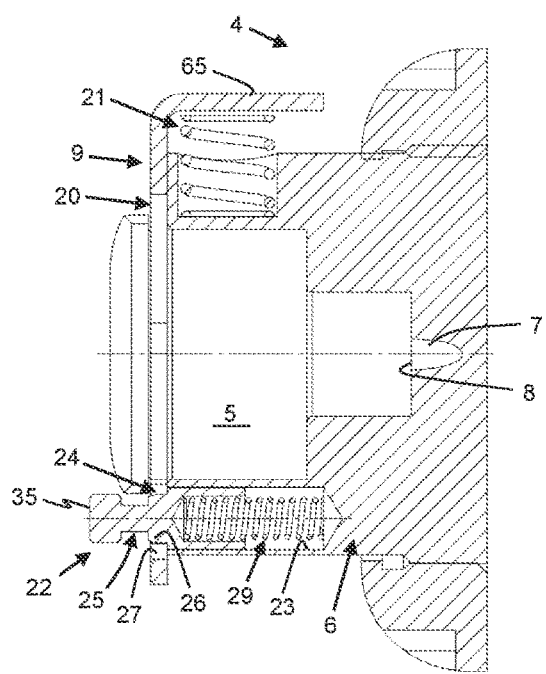
FIG. 7 shows a sectional view through the coupling piece of FIG. 6.
Figure 8:
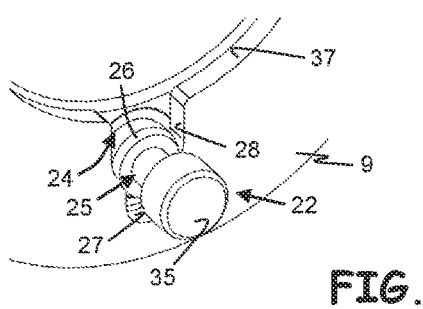
FIG. 8 shows a detailed view of the locking area of the coupling piece of FIG. 6.

The locking plate 9 and the through-opening 20 are selectively movable into the locking position and the unlocked position and can be fixed therein by the locking pin 22 and the locking opening 24. In the locking position, the coupling receptacle 5 and the coupling extension 13 and/or the coupling piece 4 and the coupling element 12 are connected to each other, in particular in a fluid-transferring manner, whereas in the unlocked position said elements 4, 12; 5, 13, are separated or separable from each other. The change between the locked position and the unlocked position shown in FIGS. 7 and 8 is caused by selective application of force to the locking plate 9 and the locking pin 22 and the movement of the locking plate 9 and the locking pin 22 caused thereby. If, for example, the locking pin 22 is moved a little way into the bore 23 when the coupling element 4 is inserted into the coupling receptacle 5, in particular by the contact surface 32, against the force of the second pretensioning element 29, the locking piece 25 of the locking pin 22 is displaced into the locking opening 24 (instead of the unlocking piece 26 located in the locking opening 24), whereby, due to the smaller diameter of the locking piece 25 and due to the pretensioning force of the first pretensioning element 21, the locking plate 9 is moved (from the unlocked position) into the locking position and the locking piece 25 is received in the locking section 27 of the locking opening 24.

The through-opening 20 of the locking plate 9 is delimited by a peripheral edge 37 which, due to the movement of the locking plate 9 into the locking position, engages in recess 36 of the coupling extension 13 inserted into the coupling element 4, whereby the coupling piece 4 and the coupling element 12 are fixed to each other. Thus, in particular in the locking position, the locking plate 9 and the through-opening 20 assume a position in which the peripheral edge 37 projects into or over the coupling receptacle 5, preferably, the through-opening 20 and the coupling receptacle 5 are arranged offset or eccentrically relative to each other, whereby the peripheral edge 37 engages recess 36. On the other hand, the locking plate 9 and the through-opening 20, in particular in the unlocked position, assume a position in which the peripheral edge 37 does not project into or beyond the coupling receptacle 5, preferably, the through-opening 20 and the coupling receptacle 5 are arranged at least approximately concentrically, whereby the coupling piece 4 and the coupling element 12 can be disengaged from each other. This described displacement of the peripheral edge 37 causes the coupling and removability of the coupling device 30 or the coupling piece 4 and the coupling element 12 by engagement or disengagement of the peripheral edge 37 with the recess 36.

As a result of a force acting on the locking plate 9, in particular its actuator 65, against the pretension of the first pretensioning element 21, the locking plate 9 moves or displaces relative to the locking pin 22, so that the latter is received by the unlocking section 28 of the locking opening 24, wherein, due to the pretensioning force of the second pretensioning element 29 and due to the larger diameter of the unlocking portion 28, the locking pin 22 partially moves away (automatically) from the bore 23 of the body 6 until its unlocking piece 26 is received in the unlocking portion 28, whereby the locking plate 9 assumes the unlocked position and is fixed therein.

The embodiments described or shown serve to illustrate the invention. The features disclosed in one embodiment are therefore not limited to that embodiment, but may be combined individually or together with one or more features of one of the other embodiments.

What is claimed is:

1. A method for preparing and/or caring for a medical or dental instrument, comprising:
   a) providing a connection adapter which is releasably connectable to a coupling end of the medical or dental instrument;
   b) connecting the medical or dental instrument via the connection adapter to a first preparation and/or care device for a medical or dental instrument;
   c) preparing and/or caring for the medical or dental instrument by the first preparation and/or care device;
   d) separating the connection adapter, jointly with the medical or dental instrument attached thereto, from the first preparation and/or care device;
   e) connecting the connection adapter, jointly with the medical or dental instrument attached thereto, to a second preparation and/or care device for a medical or dental instrument;
   f) preparing and/or caring for the medical or dental instrument by the second preparation and/or care device, wherein
   the connection adapter and the first preparation and/or care device and/or the second preparation and/or care device are connected by a plug-in coupling arrangement comprising:
   a coupling extension, and a coupling receptacle for plug-in reception of the coupling extension, wherein the coupling receptacle comprises:
   a body, in which a coupling cavity is formed,
   at least one media line for conducting a preparation and/or care medium through the body, the media line terminating in an opening on a surface of the coupling cavity,
   a locking plate movably arranged on the body, which is selectively movable into a locking position and an unlocked position,
   a through-opening being arranged in the locking plate, the through-opening being fluidically connected to the opening of the media line for the passage of the preparation and/or care medium,
   a first pretensioning element for pretensioning the locking plate,
   a locking pin which is slidably received in a bore of the body, the locking pin extending through a locking opening in the locking plate and comprising a locking piece and an unlocking piece,
   the locking opening having a locking portion and an unlocking portion, and
   a second pretensioning element for pretensioning the locking pin such that a contact end of the locking pin projects beyond the locking plate, wherein
   the locking plate and the locking pin are configured to interact in such a way that, as a result of a force acting on the contact end of the locking pin, the contact end can be moved in a direction of the bore of the body counter to the pretensioning of the second pretensioning element, until the locking piece of the locking pin is received in the locking portion of the locking opening, so that the locking plate is movable into the locking position due to the pretensioning force of the first pretensioning element, and wherein
   the locking plate and the locking pin are configured to interact in such a way that the locking plate is moved into the unlocked position by a force acting on the locking plate against the pretensioning force of the first pretensioning element, so that, due to the pretensioning force of the second pretensioning element, the contact end of the locking pin can be moved away from the bore of the body, so that the unlocking piece of the locking pin is received in the unlocking section of the locking opening and the locking plate is fixed in the unlocked position.

2. The method for preparation and/or care according to claim 1, wherein step b) comprises the following sub-steps:
   b1) connecting the medical or dental instrument to the connection adapter;
   b2) connecting the connection adapter, jointly with the medical or dental instrument attached thereto, to the first preparation and/or care device.

3. The method for preparation and/or care according to claim 1, wherein after step f), separating the medical or dental instrument from the connection adapter.

4. The method for preparation and/or care according to claim 1, wherein the medical or dental instrument comprises a hollow outer sleeve in which at least one component is arranged, wherein the preparation and/or care of the medical or dental instrument by the first preparation and/or care device and/or by the second preparation and/or care device comprises preparation and/or care of the at least one component arranged inside the hollow outer sleeve.

5. The method for preparation and/or care according to claim 1, wherein
   the coupling receptacle is arranged on the first preparation and/or care device and the second preparation and/or care device.

6. The method for preparation and/or care according to claim 1, wherein the connection adapter comprises a first end releasably connectable to the coupling end of the medical or dental instrument and a second end selectively connectable to the first preparation and/or care device for a medical or dental instrument and the second preparation and/or care device for a medical or dental instrument, wherein the second end comprises the coupling extension.

7. The method for preparation and/or care according to claim 1, wherein
   the connection adapter comprises at least one media line for a preparation and/or care medium, the at least one media line extending through the connection adapter to direct a preparation and/or care medium from the first preparation and/or care device or the second preparation and/or care device into the interior of the medical or dental instrument.

8. The method for preparation and/or care according to claim 1, wherein
   the first preparation and/or care device and the second preparation and/or care device apply different preparation and/or care processes to the medical or dental instrument.

9. The method for preparation and/or care according to claim 1, wherein
   one of the first preparation and/or care device or the second preparation and/or care device supplies a lubricant to the medical or dental instrument.

10. A plug-in coupling arrangement for connecting in a fluid transferring manner a preparation and/or care device for preparing and/or caring for a medical or dental instrument and a connection adapter connectible to the medical or dental instrument, the plug-in coupling arrangement comprising:
   a coupling extension, and a coupling receptacle for plug-in reception of the coupling extension, wherein the coupling receptacle comprises:

a body, in which a coupling cavity is formed, at least one media line for conducting a preparation and/or care medium through the body, the media line terminating in an opening on a surface of the coupling cavity, a locking plate movably arranged on the body, which is selectively movable into a locking position and an unlocked position, a through-opening being arranged in the locking plate, the through-opening being fluidically connected to the opening of the media line for the passage of the preparation and/or care medium, a first pretensioning element for pretensioning the locking plate, a locking pin which is slidably received in a bore of the body, the locking pin extending through a locking opening in the locking plate and comprising a locking piece and an unlocking piece, the locking opening having a locking portion and an unlocking portion, and a second pretensioning element for pretensioning the locking pin such that a contact end of the locking pin projects beyond the locking plate, wherein the locking plate and the locking pin are configured to interact in such a way that, as a result of a force acting on the contact end of the locking pin, the contact end can be moved in a direction of the bore of the body counter to the pretensioning of the second pretensioning element, until the locking piece of the locking pin is received in the locking portion of the locking opening, so that the locking plate is movable into the locking position due to the pretensioning force of the first pretensioning element, and wherein the locking plate and the locking pin are configured to interact in such a way that the locking plate is moved into the unlocked position by a force acting on the locking plate against the pretensioning force of the first pretensioning element, so that, due to the pretensioning force of the second pretensioning element, the contact end of the locking pin can be moved away from the bore of the body, so that the unlocking piece of the locking pin is received in the unlocking section of the locking opening and the locking plate is fixed in the unlocked position.

11. The plug-in coupling arrangement of claim 10, wherein one of the coupling extension and the coupling receptacle is arranged on the connection adapter, and the other of the coupling extension and the coupling receptacle is provided on the preparation and/or care device.

12. The plug-in coupling arrangement according to claim 10, wherein an outer diameter of the locking piece of the locking pin is smaller than the outer diameter of the unlocking piece of the locking pin, and in that an inner diameter of the locking portion of the locking opening is smaller than an inner diameter of the unlocking portion of the locking opening.

13. The plug-in coupling arrangement according to claim 10, wherein the coupling extension comprises a recess, and wherein a circumferential edge of the through-opening of the locking plate engages the recess when the coupling extension is inserted into the coupling receptacle and the locking plate assumes the locking position, so that the coupling extension and the coupling receptacle are secured to one another.

14. The plug-in coupling arrangement according to claim 10, further comprising the connection adapter connectible to the medical or dental instrument wherein a connection element for connecting a medical or dental instrument to be prepared and/or cared for is provided on the connection adapter, the connection element having a union nut with an internal thread for screwed connection with a thread of the medical or dental instrument, the union nut being displaceable along a longitudinal axis of the connection element.

15. The plug-in coupling arrangement according to claim 10, wherein a contact surface is provided on the coupling extension, wherein the contact surface is arranged in such a way that, when the coupling extension is inserted into the coupling receptacle, the contact surface exerts the force on the contact end of the locking pin to move the contact end in the direction of the bore of the body against the pretension of the second pretensioning element until the locking piece of the locking pin is received in the locking portion of the locking opening, such that the locking plate is moved into the locking position due to the pretensioning force of the first pretensioning element.

16. The plug-in coupling arrangement according to claim 10, further comprising the preparation and/or care device for preparing and/or caring for a medical or dental instrument.

17. A system for preparing and/or caring for a medical or dental instrument, comprising:

at least one preparation and/or care device for a medical or dental instrument, a connection adapter which is releasably couplable to the at least one preparation and/or care device and to a medical or dental instrument to be prepared and/or cared for by the at least one preparation and/or care device to couple the at least one preparation and/or care device and the medical or dental instrument in a fluid-transferring manner, a coupling device configured as a plug-in connector and having a coupling piece provided on the preparation and/or care device and a coupling element provided on the connection adapter to releasably couple the preparation and/or care device and the connection adapter to each other, wherein one of the coupling piece and the coupling element comprises a coupling receptacle and wherein the coupling receptacle comprises:

a body, in which a coupling cavity is formed, at least one media line for conducting a preparation and/or care medium through the body, the media line terminating in an opening on a surface of the coupling cavity, a locking plate movably arranged on the body, which is selectively movable into a locking position and an unlocked position, a through-opening being arranged in the locking plate, the through-opening being fluidically connected to the opening of the media line for the passage of the preparation and/or care medium, a first pretensioning element for pretensioning the locking plate, a locking pin which is slidably received in a bore of the body, the locking pin extending through a locking opening in the locking plate and comprising a locking piece and an unlocking piece, the locking opening having a locking portion and an unlocking portion, and a second pretensioning element for pretensioning the locking pin such that a contact end of the locking pin projects beyond the locking plate, wherein the locking plate and the locking pin are configured to interact in such a way that, as a result of a force acting on the contact end of the locking pin, the contact end can be moved in a direction of the bore of the body counter to the pretensioning of the second pretensioning element, until the locking piece of the locking pin is received in the locking portion of the locking opening, so that the locking plate is movable into the locking position due to the pretensioning force of the first pretensioning element, and wherein the locking plate and the locking pin are configured to interact in such a way that the locking plate is moved into the unlocked position by a force acting on the locking plate against the pretensioning force of the first pretensioning element, so that, due to the pretensioning force of the second pretensioning element, the contact end of the locking pin can be moved away from the bore of the body, so that the unlocking piece of the locking pin is received in the unlocking section of the locking opening and the locking plate is fixed in the unlocked position.

18. The system according to claim 17, wherein the coupling piece provided on the at least one preparation and/or care device comprises the coupling receptacle.

19. The plug-in coupling arrangement according to claim 14, wherein the union nut is displaceable between a retracted position in which the union nut is arranged closer to the coupling extension and an advanced position in which in the union nut is arranged further away from the coupling extension compared to the retracted position and in which the internal thread of the union nut can be screwed with the thread of the medical or dental instrument.

20. The system according to claim 17, wherein the at least one preparation and/or care device supplies a lubricant to the medical or dental instrument.

\* \* \* \* \*